(12) United States Patent
Nino et al.

(10) Patent No.: US 7,762,164 B2
(45) Date of Patent: Jul. 27, 2010

(54) TORQUE-LIMITING DEVICE

(75) Inventors: John Nino, Simi Valley, CA (US); David Ivinson, Camarillo, CA (US)

(73) Assignee: ECA Medical Instruments, Newbury Park, CA (US)

( * ) Notice: Subject to any disclaimer, the term of this patent is extended or adjusted under 35 U.S.C. 154(b) by 108 days.

(21) Appl. No.: 12/131,731

(22) Filed: Jun. 2, 2008

(65) Prior Publication Data

US 2009/0293687 A1 Dec. 3, 2009

(51) Int. Cl.
*B25B 23/157* (2006.01)
(52) U.S. Cl. ........................................ 81/475
(58) Field of Classification Search ........... 81/473–476, 81/58.3–58.4; 192/56.61, 69.81, 69.8; 464/39
See application file for complete search history.

(56) References Cited

U.S. PATENT DOCUMENTS

| 3,003,378 | A | * | 10/1961 | Hotchner | 81/475 |
| 3,354,754 | A | * | 11/1967 | Amtsberg et al. | 81/475 |
| 3,695,059 | A | * | 10/1972 | Laubach | 464/23 |
| 4,883,130 | A | * | 11/1989 | Dixon | 173/178 |
| 5,501,124 | A | * | 3/1996 | Ashby | 81/58.2 |
| 6,189,666 | B1 | * | 2/2001 | Willmot | 192/46 |
| 7,197,968 | B2 | * | 4/2007 | Bubel | 81/475 |
| 7,334,509 | B1 | * | 2/2008 | Gao | 81/475 |
| 7,475,619 | B2 | * | 1/2009 | Chiu et al. | 81/475 |

* cited by examiner

*Primary Examiner*—D. S Meislin
(74) *Attorney, Agent, or Firm*—Mark Krietzman; Luce, Forward, Hamilton & Scripps, LLP

(57) ABSTRACT

A torque-limiting driver has a handle, a body, a torque-limiting assembly and a work-piece engaging tip. The torque-limiting assembly includes an upper and lower shank that have a plurality of teeth circumferentially spaced. The teeth have a vertical face, and inclined face and a flat peak. The inclined face is defined by a radius of curvature that transitions to the flat peak. There is a spring for applying pressure across the upper and lower shank. The teeth engage for relative rotation when the handle is turned and disengage when a predetermined value of torque is exceeded.

7 Claims, 5 Drawing Sheets

TORQUE-LIMITING DEVICE

BACKGROUND

1. Field

This disclosure relates to a medical use driver tool and, in particular, to a torque-limiting driver that disengages at a predefined torque limit.

2. General Background

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely.

Disposable drivers are an easy to use and reliable alternative to the reusable drivers. Typically, each implant, for example, is packaged with a disposable driver designed to the implant's specifications. Once the driver has been used, it can be discarded. Thus, a surgeon can have complete confidence that the disposable driver, packaged with an implant, will impart the precise amount of torque.

These disposable drivers have been used for low torque applications. The standard torque values in these applications typically range from 4 to 20 inch-ounces. It has, however, been a challenge to develop a reliable disposable driver capable of imparting higher torques for larger applications.

SUMMARY

Torque is a measure of how much force acting on an object causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N m). The joule, which is the SI unit for energy or work, is also defined as an N m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

A disposable torque-limiting driver, in accordance with the present disclosure, has a handle, a cylindrical body and a work-piece engaging tip. Within the cylindrical body there is a torque-limiting assembly. The torque-limiting assembly includes an upper cylindrical shank and a lower cylindrical shank. The upper cylindrical shank and the lower cylindrical shank have a plurality of teeth. The teeth have a vertical face, an inclined face and a substantially flat peak. The inclined face is defined by a first radius of curvature that transitions to the substantially flat peak. The teeth are spaced circumferentially and spiral around the upper cylindrical shank and a lower cylindrical shank. There is a spring for applying pressure across the upper cylindrical shank and the lower cylindrical shank. The teeth of the upper cylindrical shank and the lower cylindrical shank engage for relative rotation when the handle is turned and disengage when a predetermined value of torque is exceeded.

DRAWINGS

Figure 1:
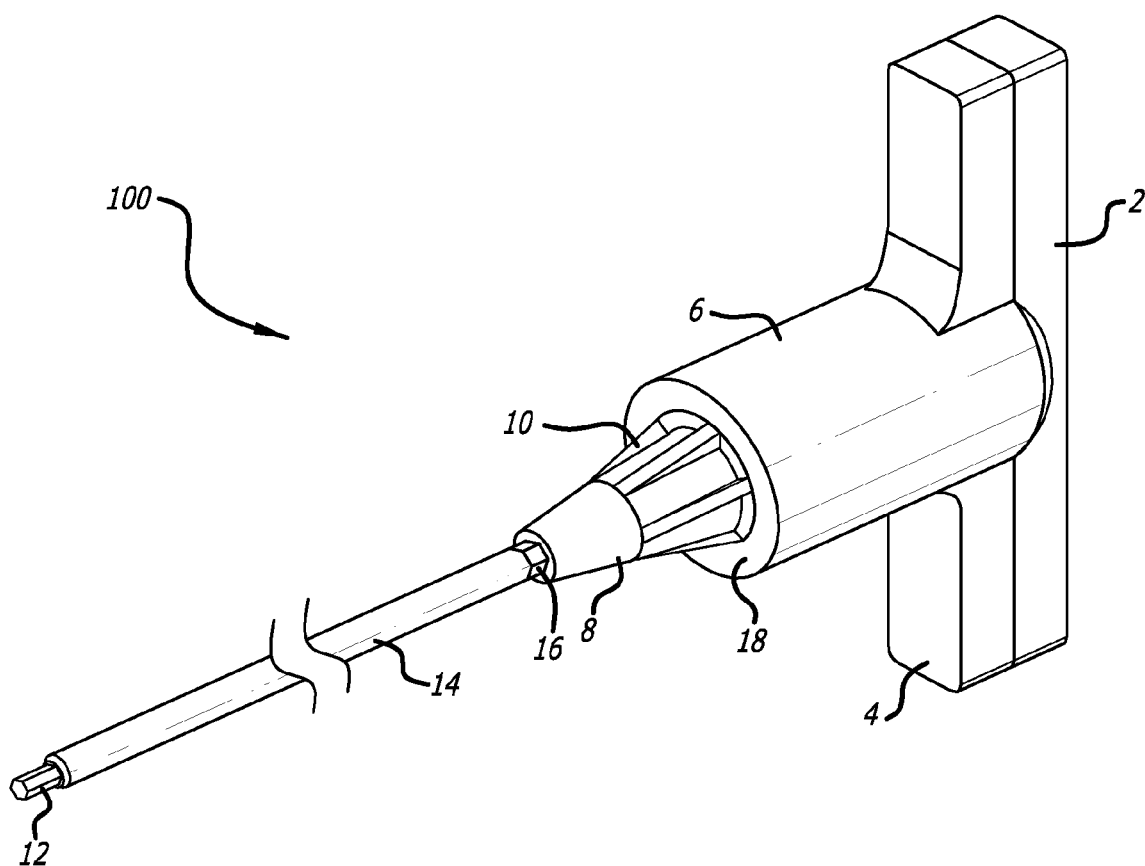
FIG. 1 is a perspective view of a driver in accordance with the present disclosure.

While the specification concludes with claims defining the features of the present disclosure that are regarded as novel, it is believed that the present disclosure's teachings will be better understood from a consideration of the following description in conjunction with the drawing figures, in which like reference numerals are carried forward.

DETAILED DESCRIPTION

Referring to FIGS. 1-8, there is a torque-limiting driver 100. The torque-limiting driver 100 has a generally T-shaped handle. The T-shaped handle includes arms 4 at one end an axially extending generally hollow cylindrical body 6, a cup 2 that covers the same end of the T-shaped handle and a cylindrical end 18 opposite the T-shaped handle on the cylindrical body 6. The cup 2 may be snap-fitted to the cylindrical body 6, or may be welded, or may be attached by any equivalent thereof and the body is preferably molded from a plastic or other economical equivalents.

At the cylindrical end 18, there is a lower shank 700 that has and annularly tapering body and a nose cone 8 along its length. The lower shank 700 may have a plurality of support flanges 10 that add strength while saving material. At one end, the lower shank 700 tapers to an axial bore 9 at the end of the nose cone 8 molded to engage a shaft 14. The shaft 14 may be hexagonal or cylindrical in transverse cross-sectional shape and is provided, at one end, with a work piece-engaging tip 12, adapted for engagement with an associated work-piece, such as a fastener or the like. The work piece-engaging tip 12 is shown to be a hex wrench, but could be a screwdriver, wrench, or any other tool arrangement. At an opposite end, the lower shank 700 has a plurality of teeth 82 arranged in a crown gear formation, a circumferential rim 31 extending radially outwardly and an internally threaded axial bore.

Figure 2:
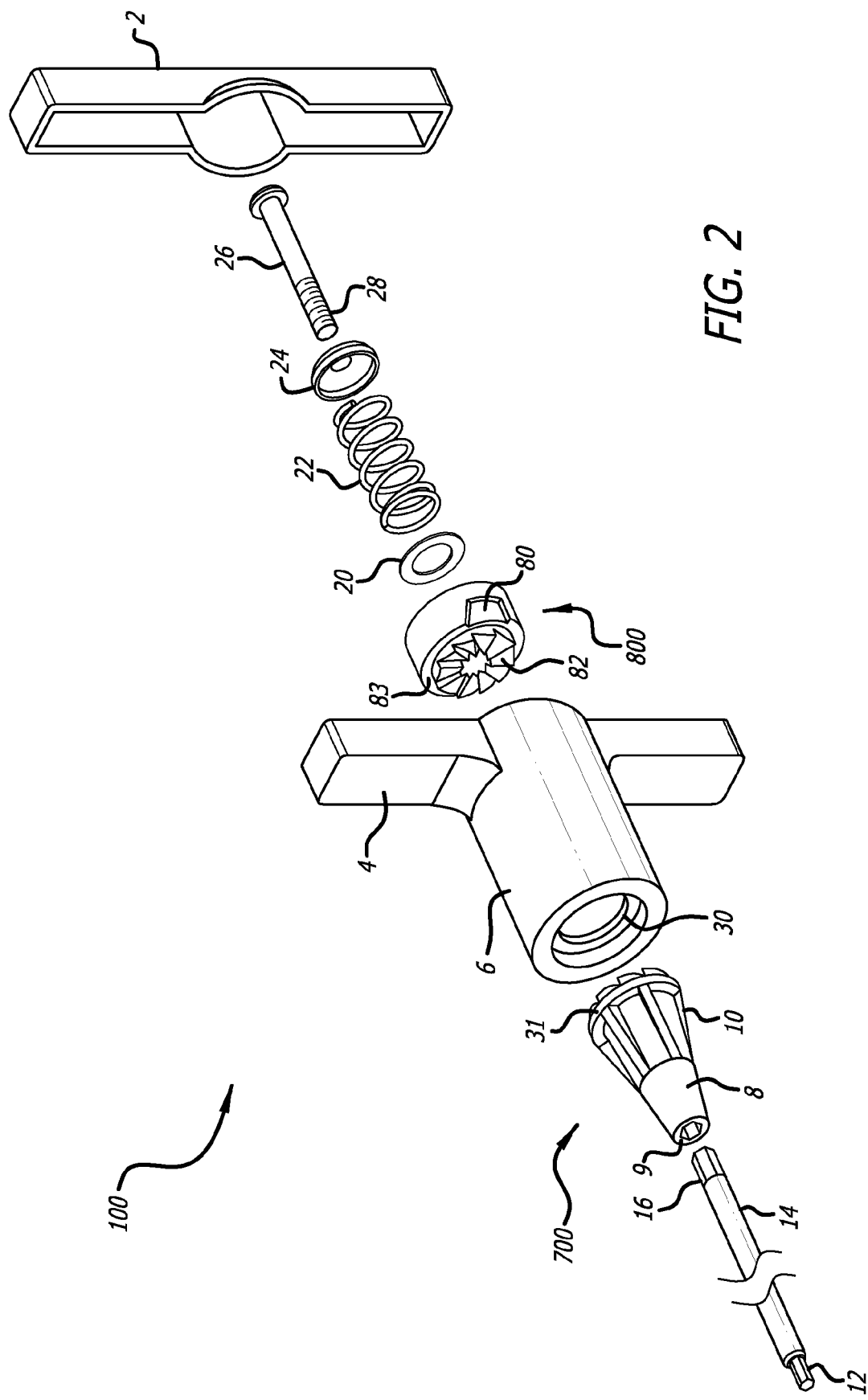
FIG. 2 is an exploded view of a driver in accordance with the present disclosure.

FIG. 2 is an exploded view of the driver 100. Inside the cylindrical body 6 a clutch assembly is disposed. The clutch assembly includes an upper shank 800 for forcibly engaging the lower shank 700. The upper shank 800 has a bottom face that has teeth 82 arranged in a crown gear formation and an annular flange or circumferential rim 83 extending radially outwardly. Shown on FIG. 5, the upper shank 800 includes an annular body or outer cylindrical shank 84, an axial bore 92 through an inner shank 86. The inner shank 86 and outer shank 84 are connected via inner supports 88, leaving the upper shank 800 substantially hollow with internal spaces 90 on a top face.

The upper shank 800 also includes at least one recess 80 on the side of the outer shank. The recess 80 is provided as a cylindrical cut, relief or recess into the side of the outer shank and maybe provided as a square or rectangular cut or the cut may have a slanted side or sides relative to the axis of the upper shank 800 as shown in FIG. 2.

In assembly, the shaft 14 is received into the axial bore 9 of the lower shank 700. A washer (not shown) maybe provided between the circumferential rim 31 of the lower shank 700 and a circumferential flange 30 extending radially inward within the hollow of the cylindrical body 6. Alternatively, the circumferential rim 31 of the lower shank 700 may be provided flush against circumferential flange 30 of the cylindrical body 6.

The opposite side of the circumferential flange 30 receives the circumferential rim 83 of the upper shank 800 allowing the teeth 82 of the lower shank 700 to engage the teeth 82 of the upper shank 800 when a torque is applied.

Figure 3:
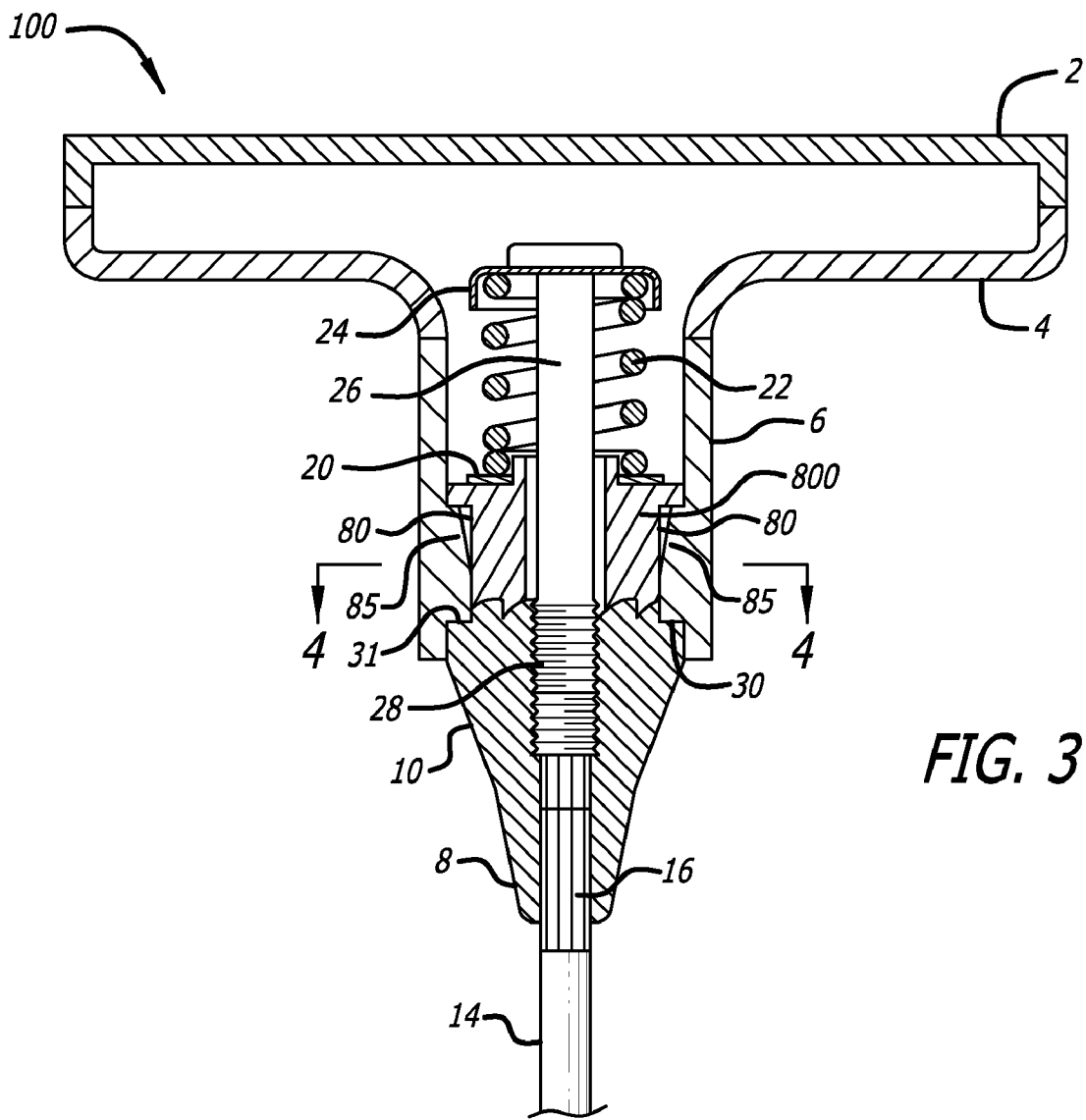
FIG. 3 is a vertical cross sectional view of a driver in accordance with the present disclosure.
Figure 4:
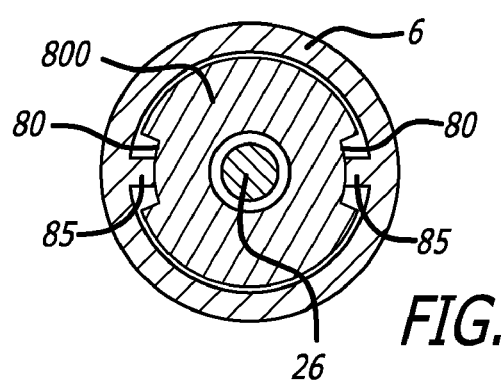
FIG. 4 is a horizontal cross sectional view of a driver in accordance with the present disclosure.
Figure 5:
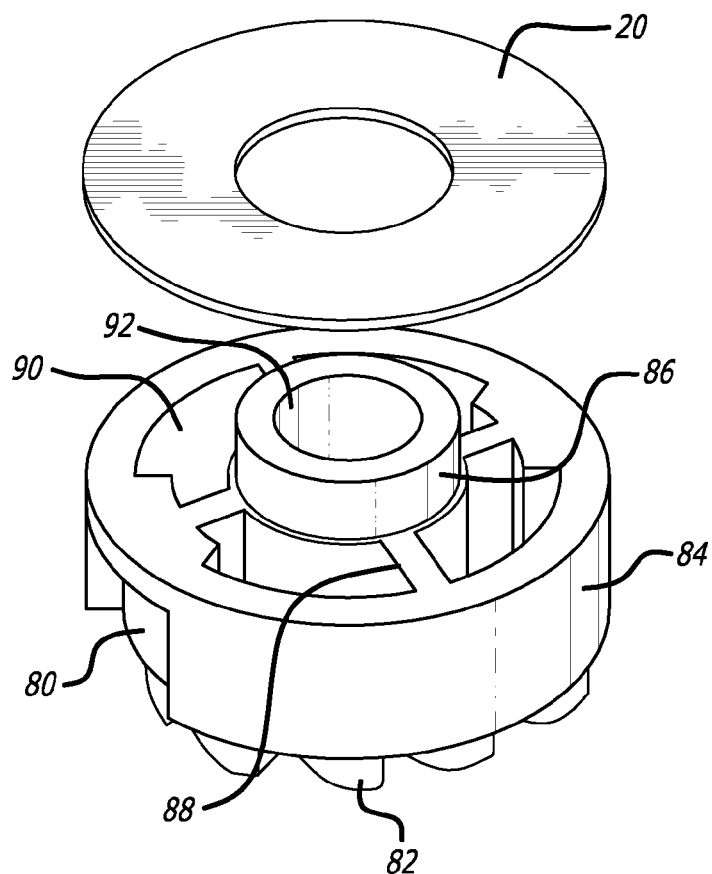
FIG. 5 is a perspective view of an upper shank in accordance with the present disclosure.

Integrally formed within the cylindrical body 6, a protrusion 85 mates with the recess 80 of the upper shank 800. FIG. 3 and FIG. 4 are cross sectional views that best illustrate the protrusion 85 in relation with the recess 80. The protrusion 85 extends inward in a radial fashion and has a length along the axis of the cylindrical body 6 for relative moveable engagement within the recess 80. This engagement provides a locking mechanism of the shaft 14 relative to the T-shaped handle via the upper shank when pressure is applied across the lower shank 700 and the upper shank 80. The recess 80 is provided circumferentially wider than the protrusion 85 for allowing the cylindrical body 6 and the T-shaped handle to rotate in reverse a predetermined distance from a locked position without subsequent reverse rotation of the work piece-engaging tip 12. Thus, the at least one recess 80 and at least one protrusion 85 lock the T-shaped in one direction providing the necessary torque to drive a fastener and allow for a predetermined amount of reverse rotation before unscrewing the fastener.

Force is applied across the lower shank 700 and the upper shank 800 via a spring 22 within the cylindrical body 6. Inside the cylindrical body 6, shown in FIG. 2 and FIG. 5, a washer 20 is provided between the upper shank 800 and the spring 22. The washer transfers pressure from the spring 22 over the top face of the upper shank 800. At an end of the spring 22 opposite the upper shank 800, a cup washer 24 and a locking screw 26 hold the spring 22 in a compressed state. The locking screw 26 has a threading 28 that engages a complementary threading within an axial bore 72 of the lower shank 700. Thus, imparting pressure between the respective teeth 82 of the lower shank 700 and the upper shank 800. The spring 22 and the locking screw 26 provide the proper tensioning and biasing for the clutch assembly and, generally, the locking screw 26 is adjustable to provide proper tension and calibration.

Figure 6:
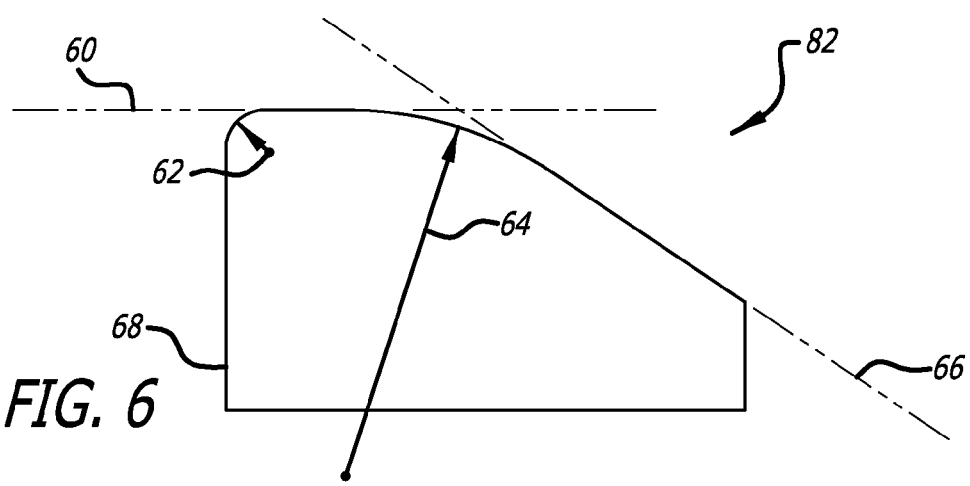
FIG. 6 is a profile of a tooth from a clutch assembly in accordance with the present disclosure.
Figure 7:
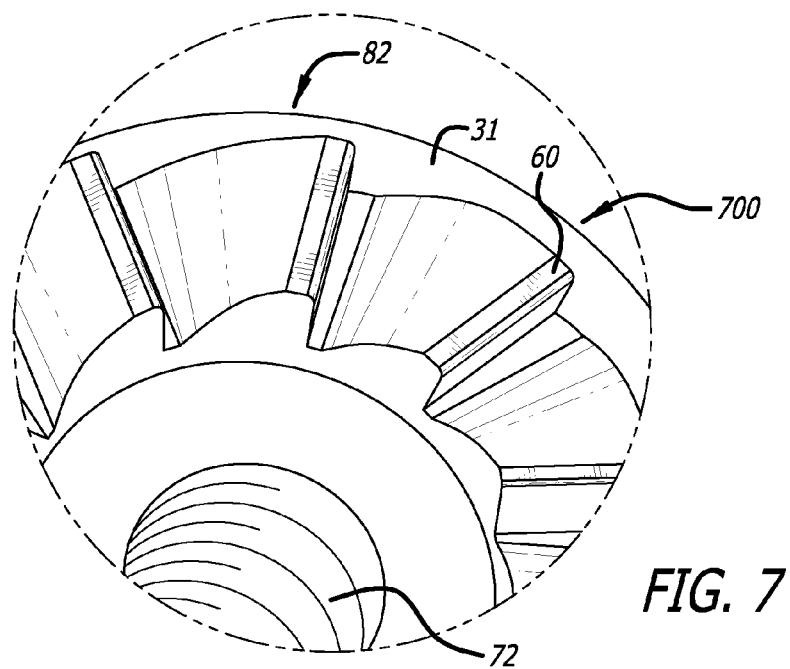
FIG. 7 is a perspective view of the teeth from a clutch assembly in accordance with the present disclosure.
Figure 8:
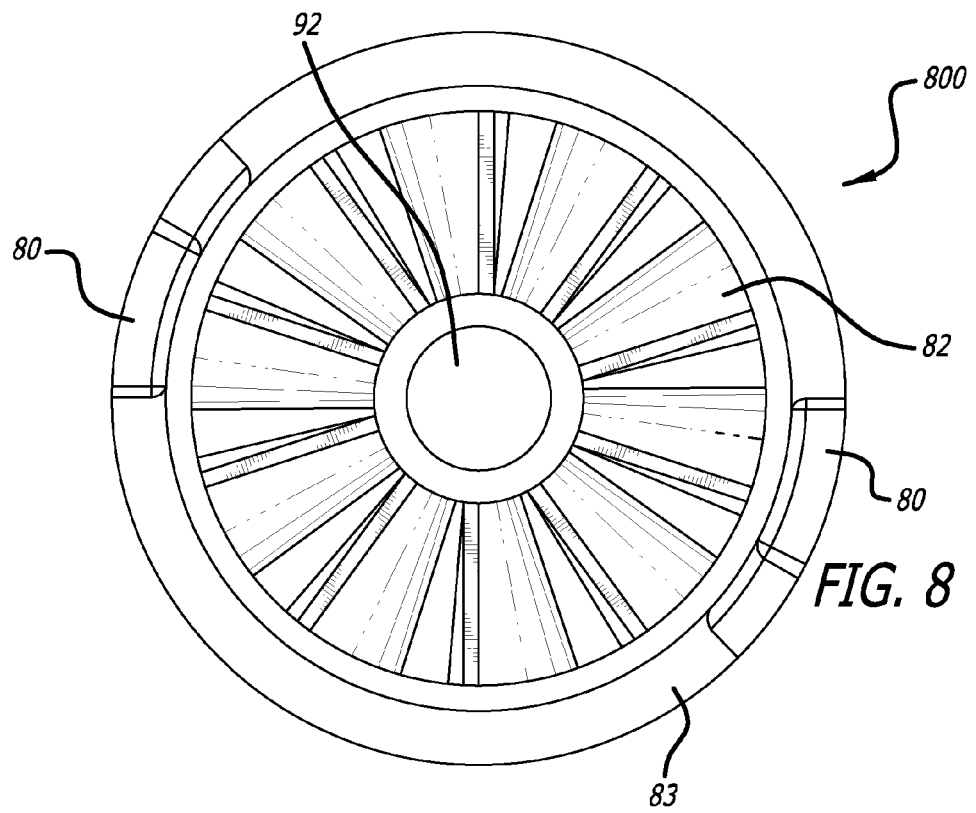
FIG. 8 is a top view of the teeth from a clutch assembly in accordance with the present disclosure.

Formed on the top face of the lower shank 700 and the bottom face of the upper shank 800 are the plurality of teeth 82 that forcibly engage to impart torque from the T-shaped handle to the work piece when a torque is applied. Referring to FIGS. 6-7, tooth 82 has an inclined face 66 that smoothly transitions to a substantially flat peak 60, via a first radius of curvature 64. The substantially flat peak 60 subsequently transitions smoothly, via a second radius of curvature, to a vertical face 68 that is substantially parallel to the axis of the lower shank 700 and the upper shank 800. The first radius of curvature is typically much larger than the second radius of curvature.

Experimental results have shown that a tooth having an inclined face that smoothly transitions to a substantially flat face is capable of imparting a substantial increase in torque to a fastener. In one experiment, a ten-fold increase in torque was observed. This increase in torque is due to the frictional forces associated with the smoothly transitioning curve of an inclined face 66 of the teeth 82.

In a simplified example, when two uniform inclines are frictionally engaged, only one static force, having a single coefficient of static force, is acting against the relative movement of the two inclines. However, when the two inclines are not uniform, more than one coefficient of static force can be observed, thus resulting in a higher disinclination to movement.

The teeth 82 are circumferentially spaced in a crown gear formation of the top face and bottom face of the lower shank 700 and the upper shank 800 respectively. The teeth 82 are also preferably configured in a spiral formation, best shown in FIG. 7. Each face of the lower shank 700 and the upper shank 800 has an inner radius and an outer radius and the teeth 82 spiral around the inner radius resulting in a larger tooth detail when viewing the tooth from the outer radius relative to the tooth detail when viewing the tooth from the inner radius. The spiral configuration of the teeth 82 can also be defined as having a longer inclined face 66 at the edge of the tooth on or near the outer radius relative to the inclined face 66 at the edge of the tooth on or near the inner radius of the lower shank 700 and the upper shank 800. Results have shown that teeth arranged in a spiral configuration provide an increased reliability and precision in torque consistency when compared to their non-spiral counterparts.

The substantially flat peak 60 of the teeth 82 can be as wide at the inner radius as they are at the outer radius. Alternatively, the substantially flat peak 60 may be wider at the outer radius and taper toward the inner radius.

The vertical faces 68 of the teeth 82 of the lower shank 700 and the upper shank 800 respectively engage when a torque is applied to prevent relative rotation of the lower shank 700 and the upper shank 800 in one direction. The inclined faces 66 engage to accommodate relative rotation of the lower shank 700 and the upper shank 800 in an opposite direction.

The extent to which the locking screw 26 is threaded into the axial bore 72 of the lower shank 700 controls the amount of compression or preload on the spring 22 which, subsequently, controls the limiting torque required to effect relative rotation of the lower shank 700 and the upper shank 800. If the locking screw 26 is threaded deeply into the lower shank 700, a higher torque will be required to disengage the teeth 82 of the lower shank 700 and the upper shank 800 than if locking screw 26 was threaded into the lower shank 700 relatively shallow.

Thus, when the driver 100 is rotated in one direction, the shaft 14 will rotate with the cylindrical body 6 and T-shaped handle until a predetermined torque is reached. When this predetermined torque is reached, a biasing force exerted by the spring 22 is overcome, allowing an inclined face 66 of the upper shank 800 to slide up a respective inclined face 66 of the lower shank 700, subsequently snapping the teeth 82 of the lower shank 700 into engagement behind a next tooth of the upper shank 800. This snapping sound is typically an audible indication to a user that a predetermined torque has been reached.

When a force beyond the required value of torque is reached, the teeth of the lower shank 700 and the upper shank 800 will continue to disengage, resulting in rotation of the handle with no further rotation of the work piece-engaging tip 12. Thus, the handle will continue to rotate, disengaging the teeth 82 with every rotational movement that will not impart continued force beyond a predefined threshold to the fastener.

When the driver 100 is rotated in the opposite direction, the T-shaped handle rotates in reverse a predetermined distance from a locked position without subsequent reverse rotation of the work piece-engaging tip 12. However, when the protrusion 85 travels the predetermined distance and locks against the opposite end of the recess 80, the driver 100 will operate as a standard driver with no torque-limiting feature since the engaging vertical face 68 will force relative rotation of the lower shank 700 and the upper shank 800 in the opposite direction without any torque-limiting feature.

The disposable torque-limiting driver of the present disclosure preferably imparts torques on the order of about 1 ounce inch to 100 inch ounces. Torques of this magnitude can be utilized in precision high torque environments such as the installation of dental, joint, vertebral implants and the like. Typically, the torque requirement is different for different operations and for different implants. Therefore, in some instances, the torques maybe around 1 inch pounds. In other instances, the predetermined torque maybe at least 30 inch pounds and yet other instances, at least 60 inch pounds, depending on an implant's specifications.

In some instances, a torque-limiting driver, such as driver 100, may be prepackaged with an implant provided for one-time use. Such an instance insures that the driver imparts the required amount of torque and has not been worn in or dulled by overuse.

In other instances, the driver 100 may be reusable. The shaft 14 may be interchangeably fixed relative to the nose cone 8 for the accommodation of multiple work piece engaging tips 12. It is also to be appreciated that the handle of the driver is not limited to a T-shape and may be provided in any other suitable configuration.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

The invention claimed is:

1. A disposable torque-limiting driver comprising:
   a handle and an axially extending cylindrical body;
   a torque-limiting assembly within the axially extending cylindrical body, the assembly comprising:
   an upper cylindrical shank;
   a lower cylindrical shank;
   wherein the upper cylindrical shank and the lower cylindrical shank have a plurality of teeth and an axial bore, the teeth have a vertical face, an inclined face and a substantially flat peak, wherein the inclined face is defined by a first radius of curvature that transitions to the substantially flat peak and wherein the teeth spiral around the axial bore; and
   a spring for applying pressure across the upper cylindrical shank and the lower cylindrical shank, wherein the teeth of the upper cylindrical shank and the lower cylindrical shank engage for relative rotation, and wherein the teeth disengage when a predetermined value of torque is exceeded;
   a locking screw threaded to mate with the lower cylindrical shank through the upper cylindrical shank;
   a work piece-engaging tip connected to the lower cylindrical shank; and
   at least one radially extending axial protrusion extending inward on an inner surface of an axially extending hollow shaft;
   wherein the upper cylindrical shank has at least one recess for receiving the at least one radially extending protrusion for locking the upper cylindrical shank relative to the lower cylindrical shank;
   wherein the at least one recess is wider than the at least one radially extending protrusion allowing the driver to rotate in reverse a predetermined distance without reverse rotation of the work piece engaging tip.

2. The disposable torque-limiting driver of claim 1, wherein the vertical face terminates in a second radius of curvature that transitions to the substantially flat peak and wherein the second radius of curvature is smaller than the first radius of curvature.

3. The disposable torque-limiting driver of claim 1, wherein the substantially flat surface is wider at the outer radius than at the inner radius and wherein the substantially flat surface is perpendicular to the axis of the upper and lower shank.

4. The disposable torque-limiting driver of claim 2, wherein the transition from the first radius of curvature and second radius of curvature to the substantially flat peak is smooth.

5. The disposable torque-limiting driver of claim 1, wherein the predetermined torque is at least 1 inch pounds.

6. The disposable torque-limiting driver of claim 1, wherein the predetermined torque is at least 30 inch pounds.

7. The disposable torque-limiting driver of claim 1, wherein the predetermined torque is at least 60 inch pounds.

* * * * *